United States Patent
Kana et al.

(10) Patent No.: US 6,916,325 B2
(45) Date of Patent: Jul. 12, 2005

(54) FEMORAL SIZING GUIDE

(75) Inventors: Richard J. Kana, Lexington, TX (US); Richard J. Taft, Austin, TX (US); Tom Riedmueller, Cedar Park, TX (US)

(73) Assignee: Zimmer Orthobiologies, Inc., Austin, TX (US)

(*) Notice: Subject to any disclaimer, the term of this patent is extended or adjusted under 35 U.S.C. 154(b) by 218 days.

(21) Appl. No.: 10/073,614

(22) Filed: Feb. 11, 2002

(65) Prior Publication Data

US 2003/0153924 A1 Aug. 14, 2003

(51) Int. Cl.⁷ ............................................. A61B 17/58
(52) U.S. Cl. ........................................................ 606/89
(58) Field of Search ............................. 606/53, 86, 87, 606/88, 89, 91, 96, 102

(56) References Cited

U.S. PATENT DOCUMENTS

| | | | |
|---|---|---|---|
| 4,487,203 A | 12/1984 | Androphy | 128/303 |
| 5,070,623 A | 12/1991 | Barnes | 33/807 |
| 5,417,694 A | 5/1995 | Marik et al. | 606/88 |
| 5,423,827 A | 6/1995 | Mumme et al. | 606/96 |
| 5,445,642 A | 8/1995 | McNulty et al. | 606/88 |
| 5,486,178 A | 1/1996 | Hodge | 606/82 |
| 5,540,696 A * | 7/1996 | Booth et al. | 606/88 |
| 5,562,675 A | 10/1996 | McNulty et al. | 606/87 |
| 5,624,444 A | 4/1997 | Wixon et al. | 606/88 |
| 5,662,656 A | 9/1997 | White | 606/88 |
| 5,688,279 A | 11/1997 | McNulty et al. | 606/88 |
| 5,688,280 A | 11/1997 | Booth, Jr. et al. | 606/88 |
| 5,688,281 A | 11/1997 | Cripe et al. | 606/88 |
| 5,728,128 A | 3/1998 | Crickenberger et al. | 606/97 |
| 5,776,137 A | 7/1998 | Katz | 606/88 |
| 5,810,831 A | 9/1998 | D'Antonio | 606/88 |
| 6,013,081 A | 1/2000 | Burkinshaw et al. | 606/88 |
| 6,024,746 A | 2/2000 | Katz | 606/88 |
| 6,056,756 A * | 5/2000 | Eng et al. | 606/87 |
| 6,059,788 A | 5/2000 | Katz | 606/88 |
| 6,077,270 A | 6/2000 | Katz | 606/88 |
| 6,096,043 A | 8/2000 | Techiera et al. | 606/88 |
| 6,193,200 B1 | 1/2001 | Cooke et al. | 600/425 |
| 6,193,723 B1 | 2/2001 | Cripe et al. | 606/88 |
| 6,258,097 B1 | 7/2001 | Cook et al. | 606/91 |
| 6,277,123 B1 | 8/2001 | Maroney et al. | 606/102 |
| 6,290,704 B1 | 9/2001 | Burkinshaw et al. | 606/88 |
| 6,458,135 B1 * | 10/2002 | Harwin et al. | 606/88 |
| 2001/0037115 A1 | 11/2001 | Maroney et al. | 606/102 |

* cited by examiner

Primary Examiner—Cary E. O'Connor
Assistant Examiner—Anu Ramana
(74) Attorney, Agent, or Firm—Jonathan D. Feuchtwang; Zimmer Technology, Inc.

(57) ABSTRACT

A sizing guide for facilitating the sizing of prosthetic devices that are implanted. The sizing guide is designed for consistent mounting at a fixed anatomical reference point to facilitate accurate and repeatable sizing estimations for a variety of bone types and sizes.

11 Claims, 11 Drawing Sheets

FEMORAL SIZING GUIDE

FIELD OF THE INVENTION

The present invention relates generally to instruments for use in orthopedic procedures, and particularly to a sizing guide to facilitate sizing of certain prosthetic implants.

BACKGROUND OF THE INVENTION

In a variety of orthopedic procedures, a section of bone tissue is removed and an orthopedic prosthesis is attached. For example, it has become relatively common to replace one or more components of a knee joint. One such prosthetic device is mounted to the distal end of a femur. Typically, several cuts are made through the bone tissue at the distal end of the femur to properly shape the bone for receipt and mounting of the prosthetic device.

However, the prosthetic device must be properly sized relative to the size of the femur to which it is attached or the strength and/or comfort of the implant can be compromised. For example, one of the sizing cuts typically is made along the anterior cortex of the femur. If the size of the implant is too small relative to the area of the cut, a "notch" is left along the bone tissue at the peripheral edge of the implanted prosthetic device. This notch can weaken the bone, making it susceptible to fracture. If, on the other hand, the implant is too large relative to the area of the cut, the anterior tip of the prosthetic device can overhang the face of the bone. This creates a gap between the implant and the bone tissue potentially resulting in reduced strength at the point of attachment between the implant and the bone tissue. Also, if the implant overhangs the bone tissue, the patient may incur soft tissue irritation.

Examples of current techniques for sizing such prosthetic devices include visually estimating the size of the cuts once a femoral cutting block or guide is fixed into position; comparing the implant to femoral drill guides; and using presurgical X-rays in conjunction with implant X-ray templates to estimate proper implant size. However, these methods involve substantial estimation by the practitioner and create difficulty in producing consistent, accurate sizing of the implant.

SUMMARY OF THE INVENTION

The following passage is intended only to provide a brief summary of limited aspects of the present invention and should not be construed as encompassing all necessary elements or steps of the inventions.

The present invention relates generally to a technique for sizing a prosthetic device. The technique utilizes a sizing guide able to assess the fit of a range of implants, such as femoral implants. The instrument is designed for consistent positioning at a fixed anatomical reference, such as the intramedullary femoral canal. Because there are established distances or measurements from the intramedullary femoral canal to various perimeter points of the implanted prosthetic device, the desired size of the implant can be readily determined when the sizing guide is consistently positioned at a fixed location with respect to an anatomical reference, e.g. the intramedullary canal.

BRIEF DESCRIPTION OF THE DRAWINGS

The invention will hereafter be described with reference to the accompanying drawings, wherein like reference numerals denote like elements, and.

DETAILED DESCRIPTION OF EXEMPLARY EMBODIMENTS

It will be appreciated that the present invention can take many forms and embodiments. Some embodiments of the invention are described so as to give an understanding of the invention. It is not intended, however, that the embodiments of the present invention that are described in this specification should limit the invention. The following describes exemplary embodiments and uses of a sizing guide that facilitates proper sizing of prosthetic devices, e.g. implants. The example described is for sizing a prosthetic device to be affixed to a distal end of a femur.

Figure 1:
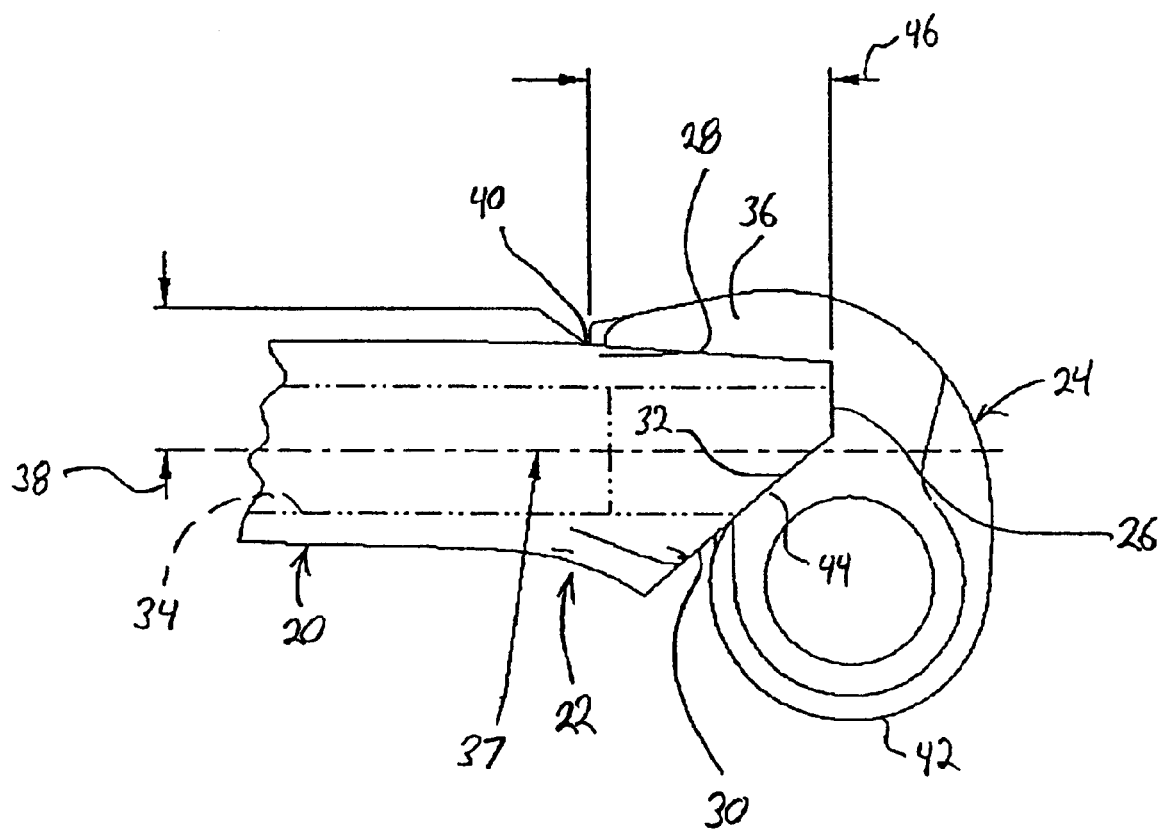
FIG. 1 is a side view of the distal end of an exemplary femur with a prosthetic device attached.

Referring generally to FIG. 1, an exemplary femur 20 is illustrated as having a distal end 22 to which a prosthetic device 24 is attached. In preparing distal end 22 for attachment of prosthetic device 24, a distal preparatory cut 26 is made to establish a generally flat plane (see also FIG. 2). Additionally, an anterior cut 28 is made generally along the anterior cortex region of femur 20 to intersect preparatory cut 26. Additionally, a posterior cut 30 is generally made at an angle that intersects a posterior side of femur 20 and preparatory cut 26, as illustrated.

If cuts 26, 28 and 30 are properly made, distal end 22 readily receives a corresponding contour 32 of prosthetic device 24. Anterior cut 28 and posterior cut 30 typically are made with the aid of a cutting block to ensure planar cuts at the appropriate angles, as known to those of ordinary skill in the art. However, the fit of prosthetic device 24 also depends on the size of femur 20 and the selected size of prosthetic device 24.

Because prosthetic device 24 is mounted on a stem extending into an intramedullary femoral canal 34, the distance to or position of various points about the implant are fixed relative to this generally centralized stem location. For example, the exemplary prosthetic device 24 comprises a flange 36 that is a fixed distance from a centerline 37 of the femoral canal 34 when the implant is attached to the femur. Thus, an anterior distance 38 measured from femoral canal 34, e.g. centerline 38, to an anterior surface or region 40 of femur 20 provides a strong indication of the desired size of prosthetic device 24.

Similarly, the distance from the femoral canal 34 to a posterior region 42 or a medial-lateral region 44 is known for an implant of a given size. Accordingly, making such sizing measurements relative to a fixed reference, such as femoral canal 34 can provide a practitioner with an indication of implant size that will provide the best fit. This, of course, facilitates selection of a properly sized cutting block and formation of proper anterior cut 28 and posterior cut 30.

Additionally, in the exemplary prosthetic device 24, flange 36 has a known flange height 46. This flange height distance also can be measured from known reference points, such as preparatory cut 26 and femoral canal 34 to ensure that a properly sized prosthetic device is selected. If, for example, the selected prosthetic device 24 is too small, fitment problems result. For example, if anterior cut 28 extends beyond flange 36 a "notch" is left in the bone tissue along the periphery of flange 36. This notch can weaken the bone, rendering it susceptible to future fracture. Even if the practitioner avoids notching by blending the cut, there may still exist the problem of insufficient cortical bone to support the implant. If, on the other hand, the selected implant is too large, the anterior region of prosthetic device may overhang the face of preparatory cut 26 resulting in a gap between anterior cut 28 and the implant. This can reduce the strength of the attachment and also cause soft tissue irritation to the patient. A prosthetic device 24 that is too large relative to femur 20 also can overhang the bone tissue at medial-lateral regions 44, potentially leading to problems such as tissue irritation. Furthermore, an oversized implant can result in location of posterior region 42 at a distant too great from the centerline 37 of the femoral canal.

Figure 2:
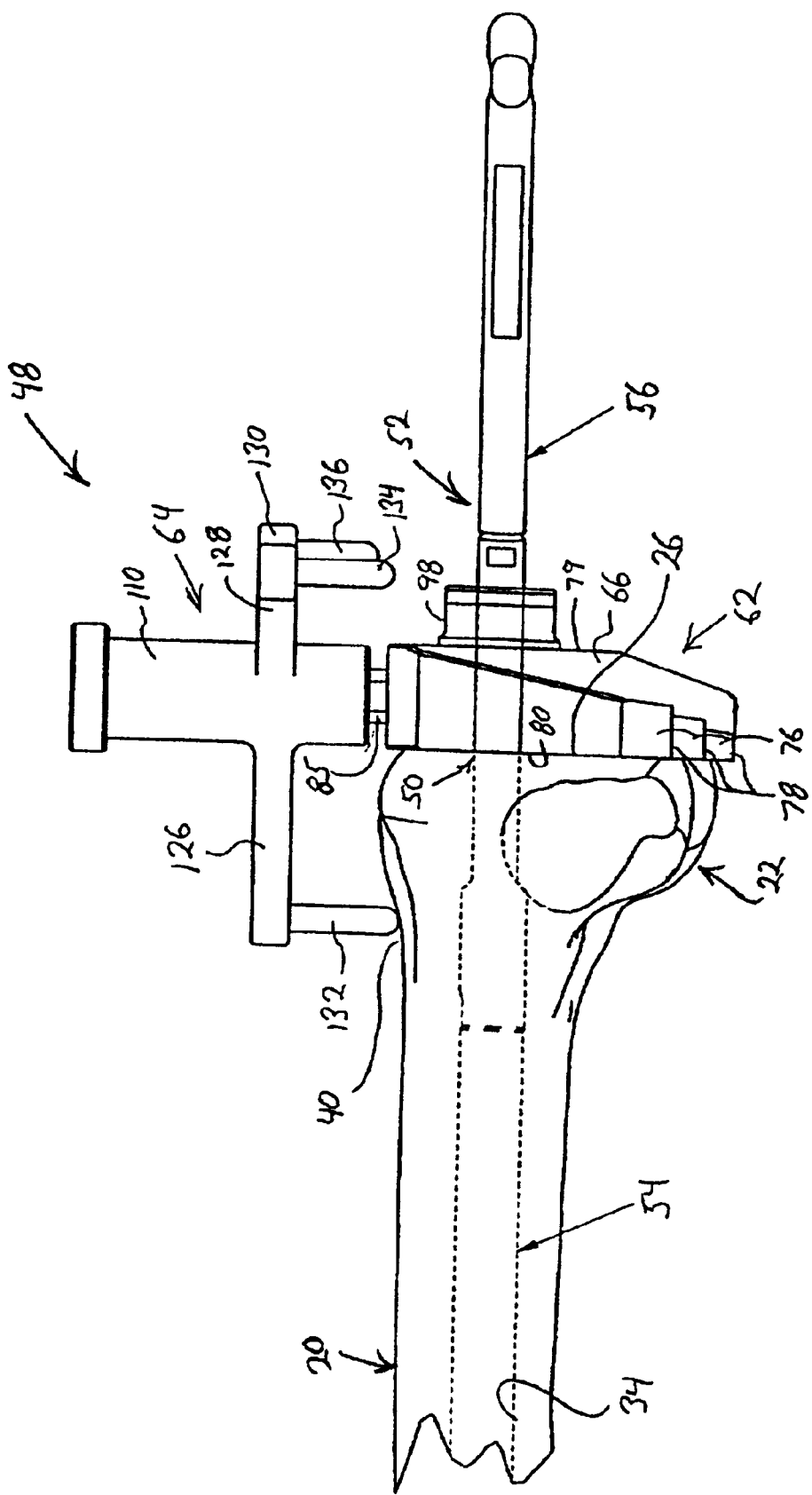
FIG. 2 is a side view of the femur illustrated in FIG. 1 with a sizing guide mounted thereto prior to shaping the femur for receipt of the prosthetic device.
Figure 3:
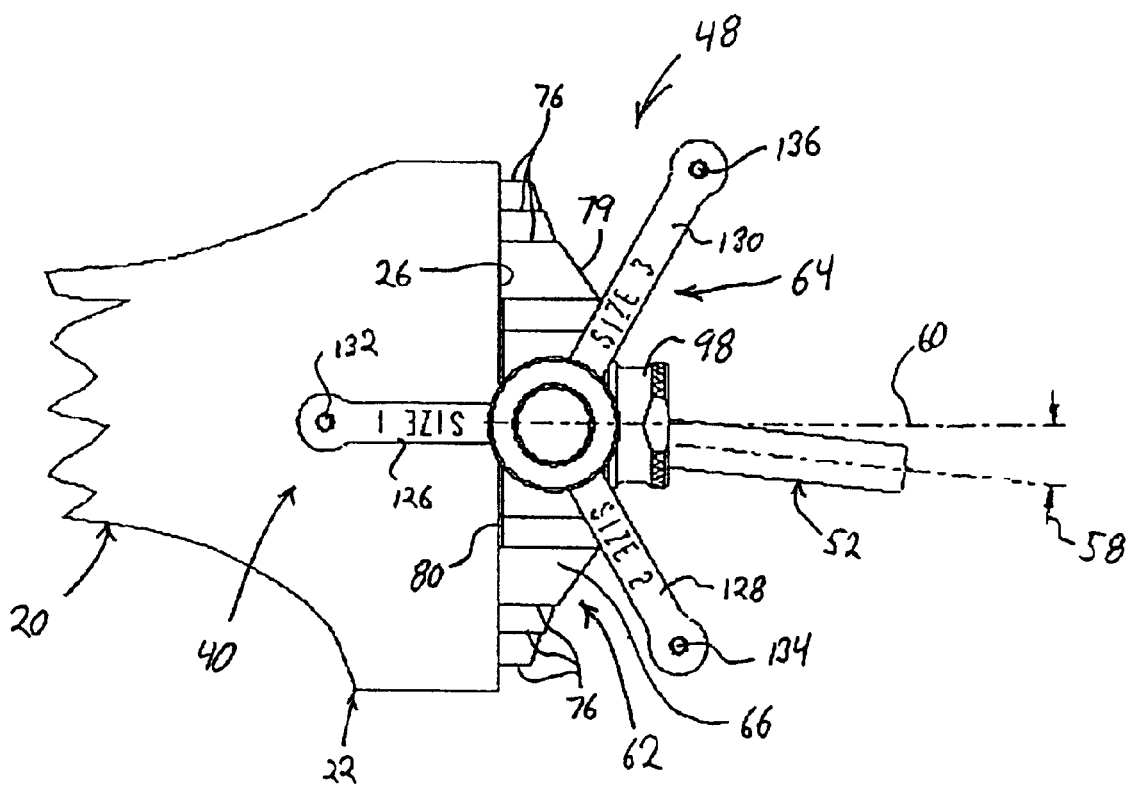
FIG. 3 is a top view of the sizing guide illustrated in FIG. 2 positioned adjacent the distal fend of a femur.

As illustrated in FIGS. 2 and 3, an exemplary sizing guide 48 is positioned adjacent distal end 22 at a fixed location relative to a fixed anatomical region 50, in this case, femoral canal 34. Thus, a variety of sizing measurements may be made that are based on or "driven from" the femoral canal 34.

In the example illustrated, sizing guide 48 is mounted over a rod 52 extending from femoral canal 34. One exemplary rod 52 comprises a trial stem 54 positioned within femoral canal 34 and attached to a trial stem adapter 56 that extends outwardly from femoral canal 34. Sizing guide 48 is slid along rod 52 into contact with preparatory cut 26 of femur 20. Once disposed at this fixed position with respect to intramedullary femoral canal 34, a variety of sizing determinations may be made.

It should be noted that in at least some implant designs, the implant stem is disposed at a slight angle with respect to certain mounting surfaces of the implant. Consequently, preparatory cut 26 is formed at a similar angle with respect to femoral canal 34. Accordingly, sizing guide 48 may be designed to receive rod 52 therethrough at such an angle (labeled angle 58) with respect to a longitudinal axis or centerline 60 of sizing guide 48, as illustrated in FIG. 3. An exemplary angle is approximately 6 degrees, however, other angles may be appropriate depending on implant design and bone characteristics.

Figure 4:
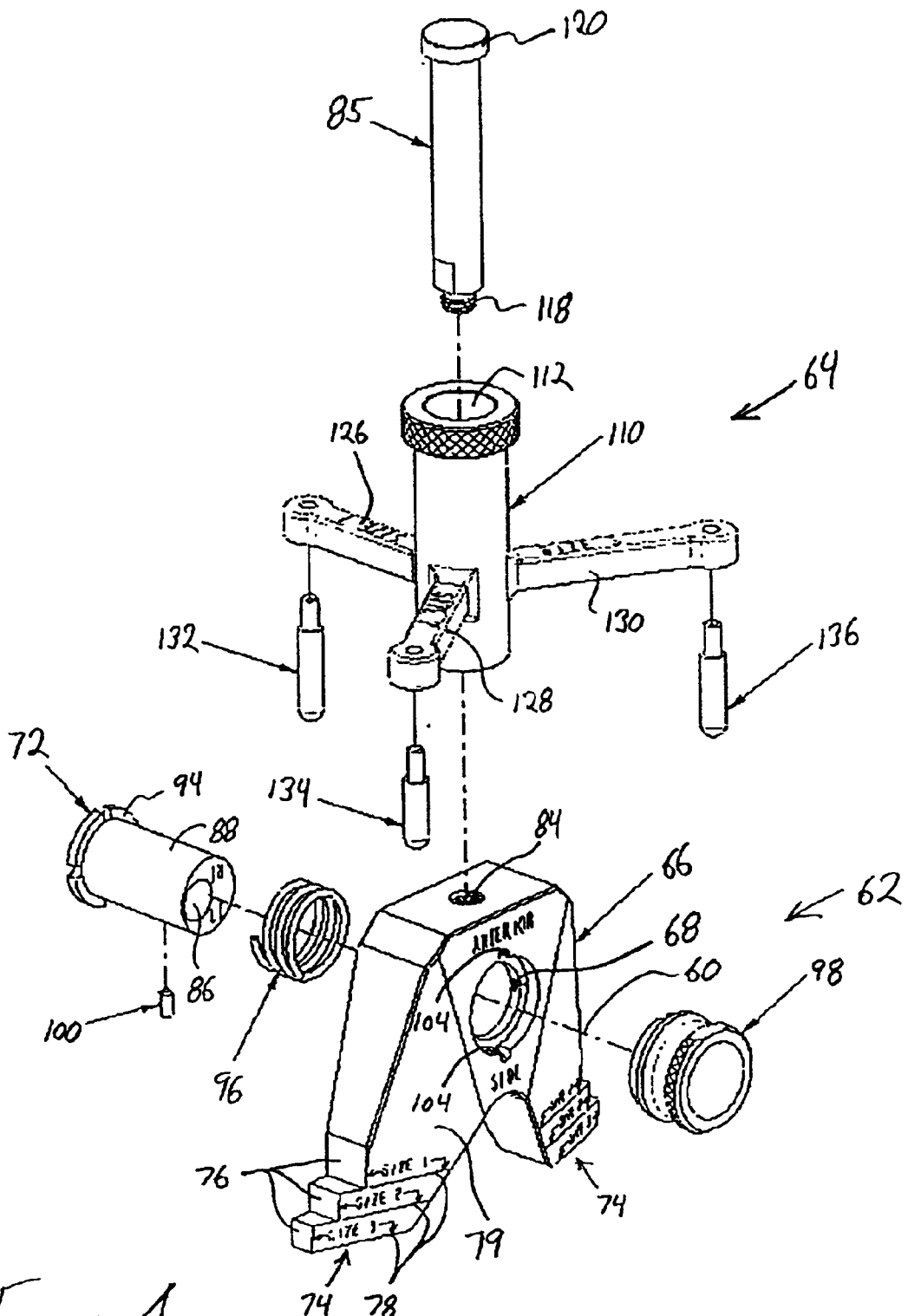
FIG. 4 is an exploded view of the sizing guide illustrated in FIGS. 2 and 3.

With additional reference to FIG. 4, sizing guide 48 generally comprises a sizing block 62 and a stylus member 64 rotatably mounted to sizing block 62. When sizing block 62 is positioned against distal end 22 of femur 20, stylus member 64 may be rotated to one or more of a plurality of positions to generally determine anterior distance 38 and thus the optimal size of prosthetic device 24.

Figure 5:
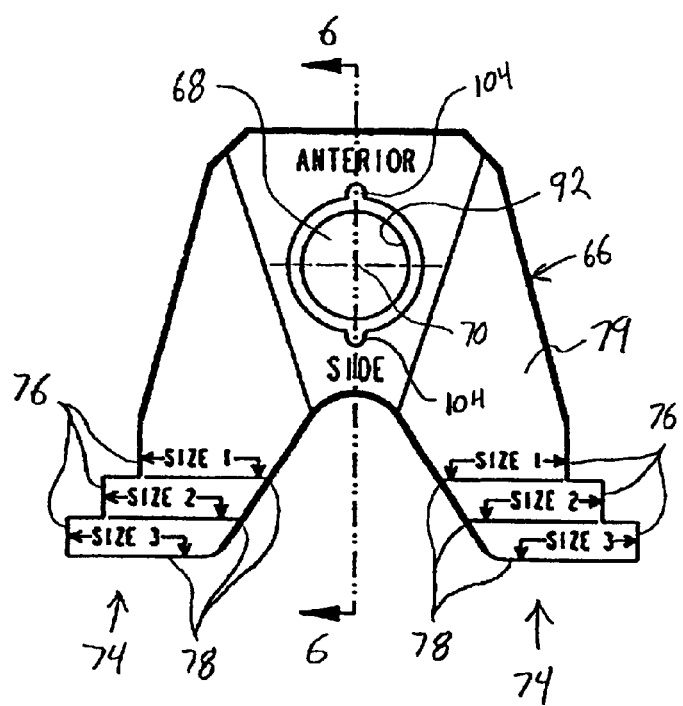
FIG. 5 is a front view of a sizing block used in the sizing guide illustrated in FIG. 4.

Although sizing block 62 may have a variety of sizes and configurations, the exemplary sizing block comprises an A-shaped frame 66, as best illustrated in FIG. 5. An opening 68 extends longitudinally through frame 66 along longitudinal axis 60 of sizing block 62. Opening 68 is sized to receive a bushing 72, as described in greater detail below.

Figure 6:
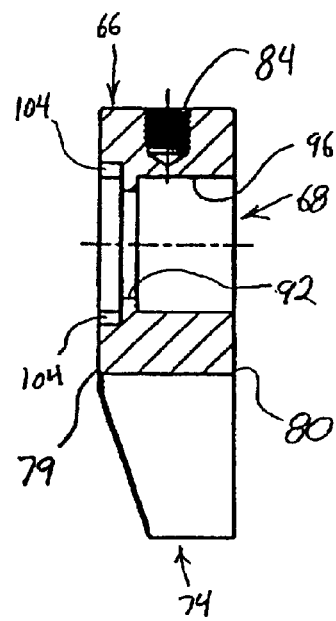
FIG. 6 is a cross-sectional view taken generally along the line 6—6 of FIG. 5.

Frame 66 also comprises a pair of legs or extensions 74 that extend generally in a direction towards the posterior region of femur 20 when sizing guide 48 is positioned as illustrated in FIG. 2. Each extension 74 includes medial-lateral sizing features 76 and posterior sizing features 78. Additionally, frame 66 comprises a generally flat engagement surface 80, as best illustrated in FIG. 6. Engagement surface 80 is designed to abut against preparatory cut 26, as illustrated in FIGS. 2 and 3.

Sizing features 76 and 78 are arranged as outwardly descending steps. The sides of each step provide a medial-lateral measurement indicative of an implant size, and the bottom of each step provides a posterior measurement indicative of the posterior extent of an implant having a given size. The size indications are provided on a visible surface 79 of frame 66.

Frame 66 further comprises a threaded opening 84. Opening 84 is designed to threadably receive a mounting pin 85 (see FIG. 4) by which stylus member 64 is mounted to sizing block 62.

Figure 8:
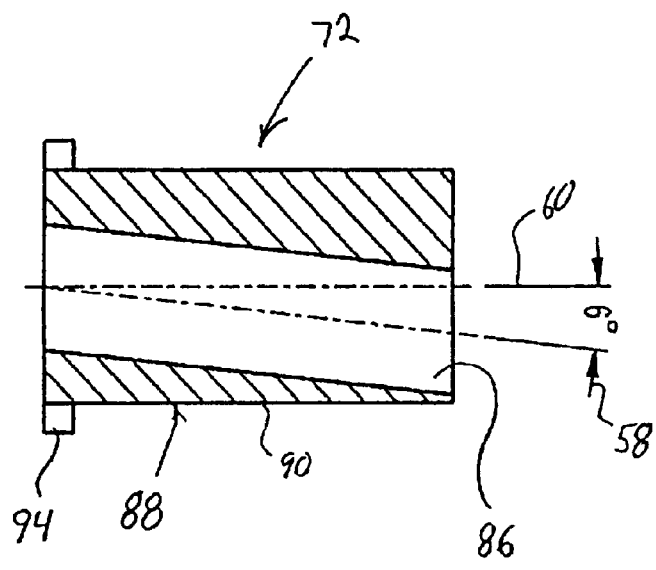
FIG. 8 is a cross-sectional view taken generally along line 8—8 of FIG. 7.
Figure 7:
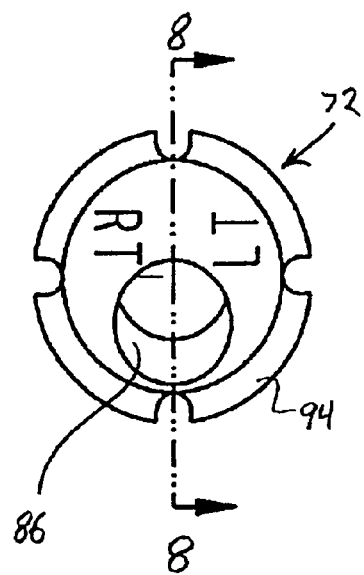
FIG. 7 is a front view of a bushing received by the sizing block.

Frame 66 also receives rod 52, e.g. trial stem adapter 56, therethrough when engagement surface 80 is moved into position adjacent distal end 22 of femur 20. In the particular embodiment illustrated, rod 52 is slidably received through a bushing openings 86 of bushing 72. Bushing 72 is best illustrated in FIGS. 7 and 8. Bushing opening 86 passes longitudinally through bushing 72 and may be disposed at angle 58, e.g. a 6 degree angle, with respect to longitudinal axis 60. In the embodiment illustrated, longitudinal axis 60 is the longitudinal axis of bushing 72 as well as the overall sizing block 62 and is generally perpendicular to engagement surface 80. Thus, as sizing block 62 is slid onto rod 52, sizing block 62 and specifically engagement surface 80 are positioned at the angle 58 with respect to femoral canal 34.

In one exemplary embodiment, bushing 72 is designed for rotatable movement such that bushing opening 86 may be moved between at least two angular positions. For example, if bushing 72 is rotated 180°, angle 58 is formed on a directly opposed side of longitudinal axis 60. This allows easy adaptation of sizing guide 48 for use on either the left femur or the right femur of a patient undergoing the orthopedic procedure. This adaptability can be achieved by permitting the rotation of bushing 72 between two or more locked positions.

Figure 9:
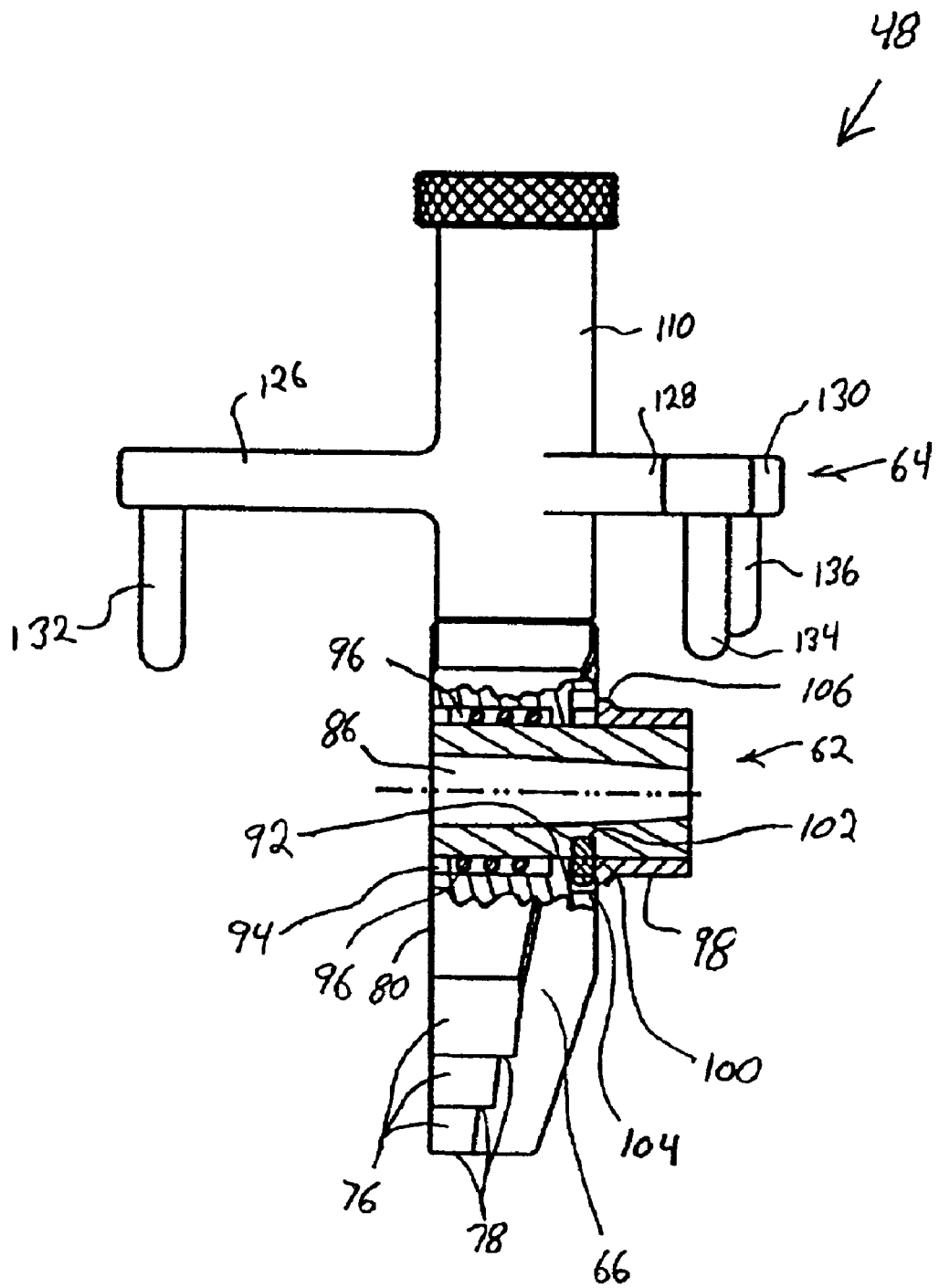
FIG. 9 is a partial cross-sectional view of the sizing guide, illustrating the bushing of FIG. 7 positioned within the sizing block of FIG. 5.

The exemplary bushing 72 comprises a barrel portion 88 having a generally smooth outer surface 90 that is rotatably received in a narrowed portion 92 of opening 68 (see also FIG. 9). Bushing 72 further comprises an annular flange 94 that extends radially outwardly from outer surface 90 to prevent movement past narrowed portion 92. Between narrowed portion 92 and engagement surface 80, opening 68 comprises an expanded region 96 sized to receive both barrel portion 88 and a surrounding spring member 96, as best illustrated in FIG. 9. An exemplary spring member 96 is a coil spring that fits around barrel portion 88 within expanded region 96 while being axially trapped between narrowed portion 92 of opening 68 and annular flange 94 of bushing 72.

Bushing 72 is held within opening 68 by a cap member 98 positioned on an opposite side of narrowed portion 92 from the flange 94 and affixed to barrel portion 88. Cap member 98 may be affixed to barrel portion 88 in a variety of ways, including threaded engagement, press fitting, adhesives, weldments, or one or more fasteners. For example, a pin 100 may be radially inserted through a corresponding opening in cap member 98 and threaded or pressed into a radial opening 102 formed through outer surface 90 of bushing 72. Preferably, pin 100 extends radially outward from cap member 98 for receipt in corresponding recesses 104, as best illustrated in FIGS. 5, 6 and 9. In the embodiment illustrated, frame 66 comprises two recesses 104 disposed on generally opposite sides of opening 68. This placement of recesses 104 permits the 180° rotation of bushing opening 86 to accommodate orthopedic procedures on either leg of the patient.

To adjust the angle of bushing opening 86, cap member 98 is gripped and bushing 72 is pulled against the spring bias of spring member 96 until pin 100 clears the corresponding recess 104. Cap member 98 is then used to rotate bushing 72 and bushing opening 86 to the next predetermined angle or position where pin 100 is aligned with a different, e.g. opposite, recess 104. The operator then releases cap member 98 and allows spring member 96 to move pin 100 towards and into the desired recess 104. In the example illustrated, cap member 98 comprises an annular flange 106 that prevents spring member 96 from moving bushing 72 beyond a flush position with respect to engagement surface 80.

Figure 10:
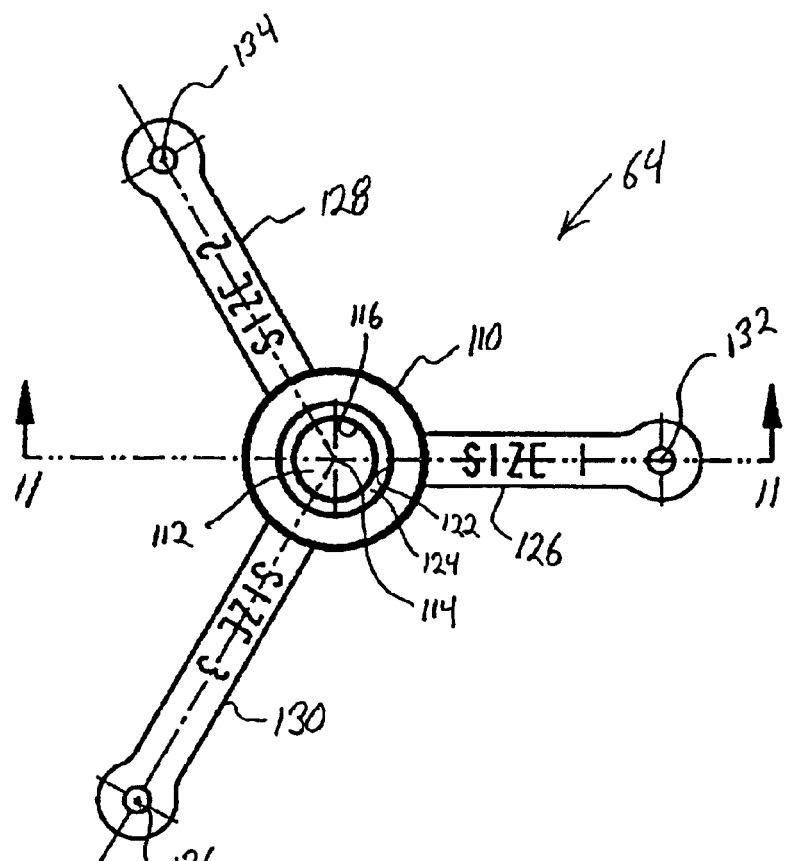
FIG. 10 is a top view of an exemplary stylus that may be rotatably mounted to the sizing block of FIG. 5.
Figure 11:
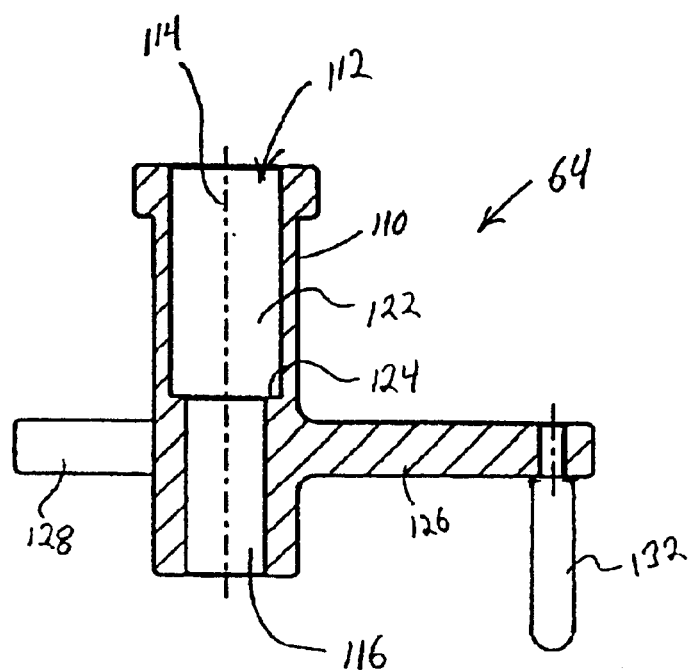
FIG. 11 is a cross-sectional view taken generally along line 11—11 of FIG. 10.

Referring generally to FIGS. 10 and 11, one exemplary embodiment of stylus member 64 is illustrated. Stylus member 64 comprises a generally central hub 110 having an opening or passage 112 therethrough. Passage 112 extends generally along an axis 114 disposed at the radial center of hub 110.

Passage 112 has a narrow portion 116 sized to slidably receive mounting pin 85 when mounting pin 85 is engaged with threaded opening 84 of frame 66 via a mounting pin threaded portion 118 (see FIG. 4). However, narrow portion 116 is not large enough to permit the passage of a mounting pin head 120, thus preventing inadvertent separation of stylus member 64 from sizing block 62.

Passage 112 is further defined by a broad portion 122 separated from narrow portion 116 by an annular shoulder 124. Broad portion 122 is large enough to receive mounting pin head 120 which is slidably disposed within broad portion 122 at a distance from shoulder 124 when mounting pin 85 is secured to sizing block 62. This permits stylus member 64 to be lifted or otherwise moved away from sizing block 62 without permitting complete separation of stylus member 64 from sizing block 62.

Extending outwardly from hub 110 are a plurality of arms 126, 128 and 130. Each arm is of a different length and corresponds to a prosthetic device of a given size. Specifically, each arm length generally corresponds to flange height 46 indicates the periphery or height of flange 36 when sizing guide 48 is mounted against femur 20. Although three arms are illustrated, the number of arms may be changed to represent a lesser or greater number of implant size selections. As illustrated best in FIG. 3, a given arm, e.g. arm 126, can be rotated back and forth across femur 20 to provide the practitioner with a general idea as to the reach or height of flange 36 along anterior region 40 when prosthetic device 24 is attached to femur 20.

One of the functions of stylus member 64 is to help determine anterior distance 38 and to correlate this distance to a specifically sized prosthetic device 24. To accomplish this aspect of sizing the prosthetic device, a plurality of pins 132, 134 and 136 are mounted to the outlying ends of arms 126, 128 and 130, respectively. Each pin is oriented to extend from its corresponding arm towards anterior region 40 of femur 20 when positioned adjacent anterior region 40. The length of each pin is different and corresponds to a prosthetic device having a given size, as explained in greater detail below.

It should be noted that the use of arms 126, 128, 130 and pins 132, 134, 136 can be replaced or supplemented with other types of measuring tools by which a practitioner is able to determine anterior distance 38 and its correlation to a prosthetic device of a given size. For example, hub 110 can be mounted on or adjacent a scale, and a single pin can be moved along the anterior region 40 of femur 20. As the pin is moved along the bone tissue, hub portion 110 rises or falls along the scale which is appropriately marked for correlation to prosthetic devices of specific sizes. The measurement, and resultant implant size determination, also can be made with a variety of sensors able to determine the desired anterior distance. Accordingly, stylus member 64 is amenable to a variety of alterations depending on the application and the technology available.

Figure 12:
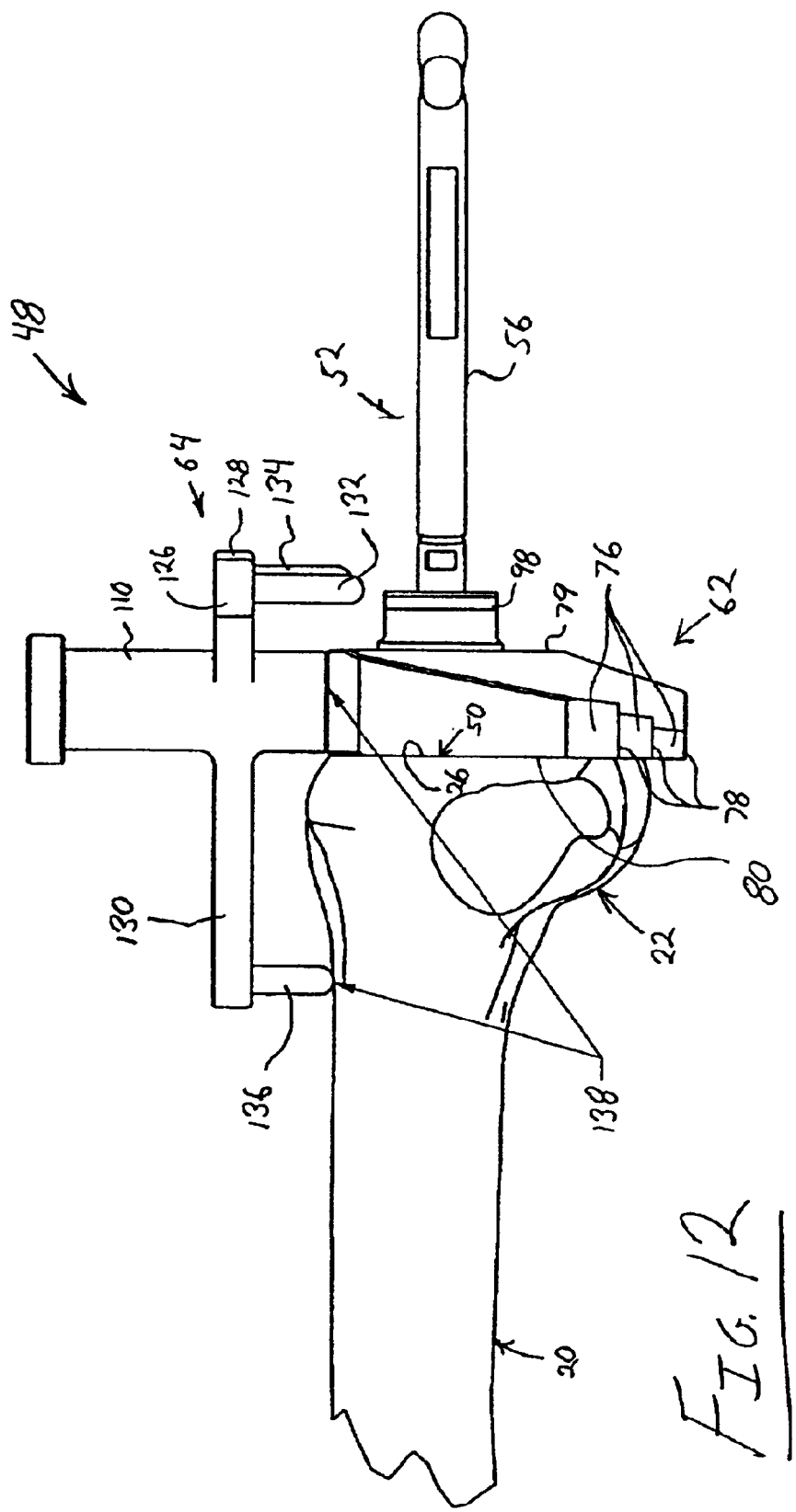
FIG. 12 is a side view of the sizing guide positioned against a femur to determine the proper implant size.
Figure 13:
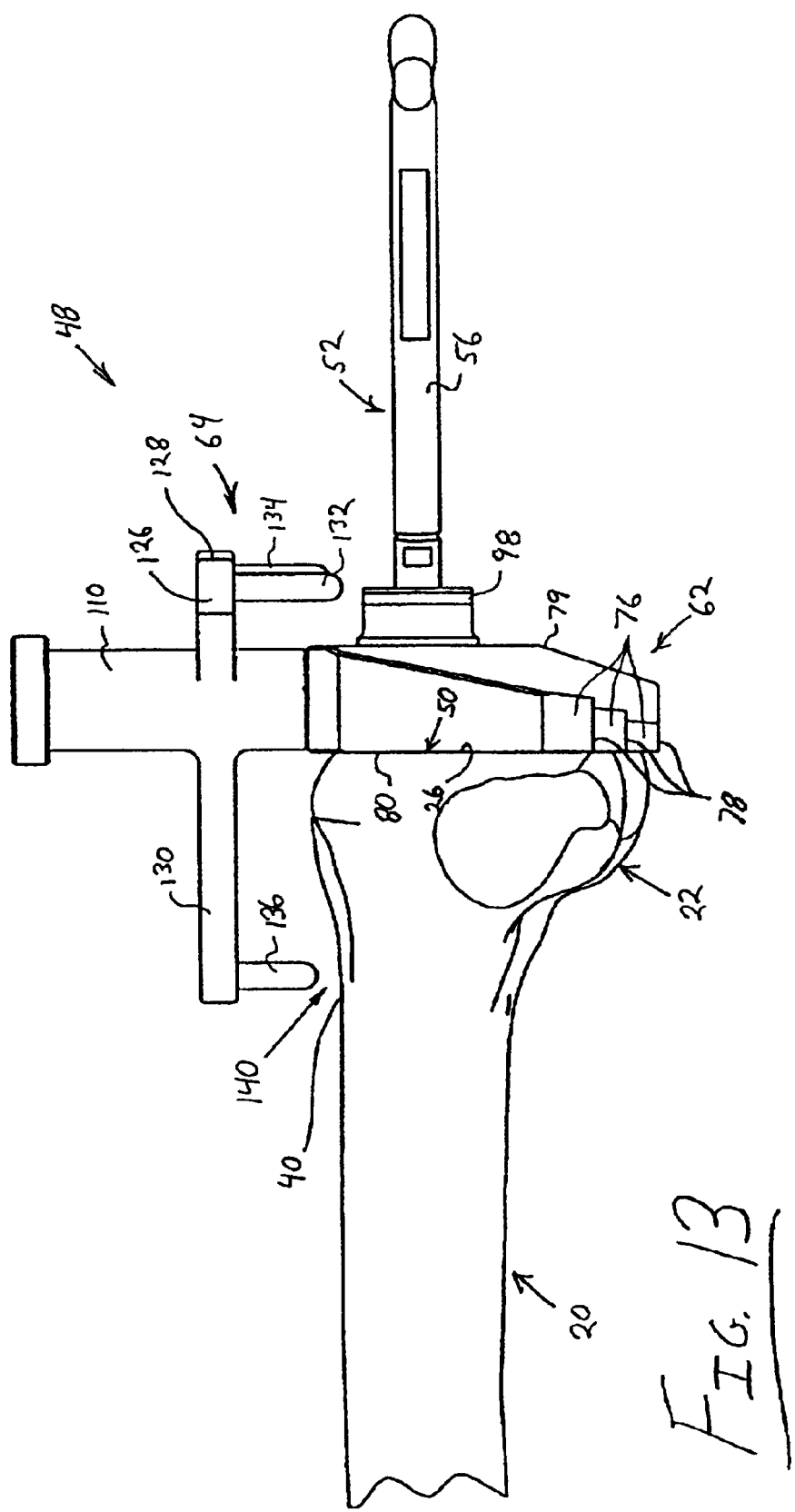
FIG. 13 is a view similar to FIG. 12 with the sizing guide indicating an implant size that would be too large.
Figure 14:
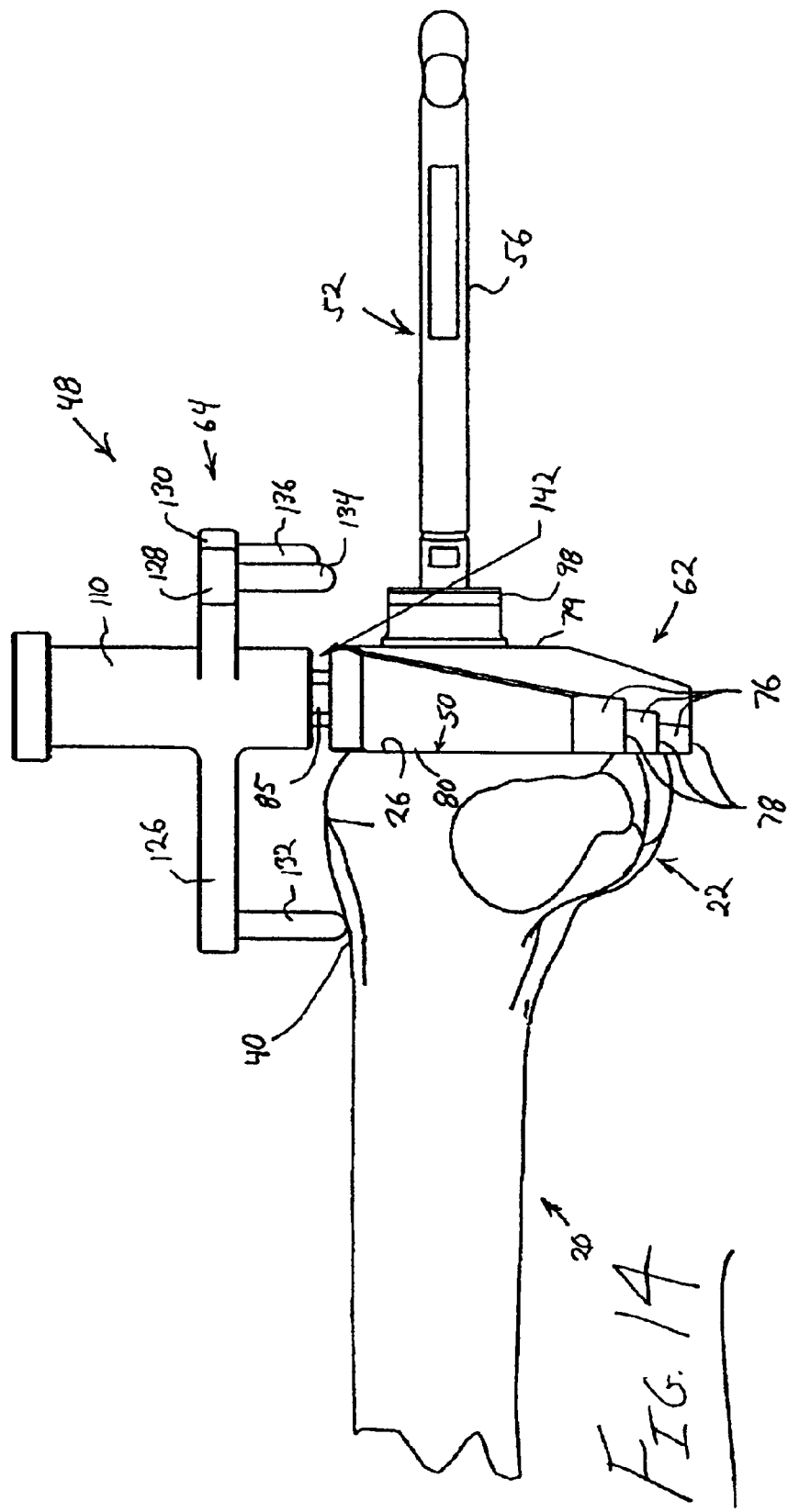
FIG. 14 is a view similar to FIG. 12 in which the sizing guide is indicating an implant size that would be too small.

Operation of sizing guide 48 is explained with reference to FIGS. 12, 13 and 14. In FIG. 12, sizing guide 48 has been slid over rod 52, e.g. trial stem adapter 56, via insertion of rod 52 through bushing opening 86. Sizing block 62 is moved along rod 52 until engagement surface 80 abuts femur 20 at preparatory cut 26. To ensure proper engagement between surface 80 of sizing block 62 and surface 26 of femur 20, bushing 72 is rotated to the appropriate position to compensate for the orientation of preparatory cut surface 26 with respect to femoral canal 34.

Once sizing block 62 is appropriately positioned, stylus member 64 is rotated until one of the pins 132, 134 and 136 is adjacent anterior region 40 of femur 20 without substantially lifting hub 110 away from sizing block 62, as illustrated in FIG. 12 by indicator arrows 138. In this example, sizing guide 48 indicates the optimal size for prosthetic device 24 is the size that corresponds to pin 136, e.g. a size 3, as opposed to a size 2 (corresponding to pin 134) or a size 1 (corresponding to pin 132).

The other sizing features can be used as supplemental or alternative techniques for determining and/or verifying the prosthetic device size selection. Specifically, the length of arm 130 and the longitudinal positioning of pin 136 along anterior region 40 provides the practitioner with an indication of flange height for the prosthetic device of a given size, i.e. size 3. The arc traversed along anterior region 40 as arm 130 rotates pin 136 across this region provides an indication of where the perimeter of flange 36 would lie when prosthetic device 34 is attached to femur 20.

Additionally, medial-lateral sizing feature 76 provides the practitioner with an indication of the medial and lateral extent of a specifically sized prosthetic device. This can be used, for example, to confirm whether the implant size indicated by pin 136 is also appropriate given the medial-lateral extent of distal end 22 of femur 20.

Similarly, posterior sizing feature 78 can be used to provide the practitioner with an indication of the posterior extent of prosthetic device 24 so he or she can assess whether the size selected, e.g. size 3, is appropriate for femur 20. Each of the sizing features, pins 132, 134, 136; arms 126, 128, 130; medial-lateral sizing feature 76; and posterior sizing features 78 are based on or "driven" from the fixed anatomical reference 50 of femur 20, e.g. the medullary femoral canal 34.

When pin 136 is proximate anterior region 40 and minimal or no gap exists between hub 110 and sizing block 62, as illustrated in FIG. 12, the practitioner has a primary indication of a properly sized prosthetic device 24. However, if a substantial gap 140 exists between a given pin, e.g. pin 136, and anterior region 40 of femur 20, (see FIG. 13) the practitioner is provided with an indication that the implant corresponding to pin 136 is too large for femur 20. In other words, an implant having a smaller size would be more desirable.

Alternatively, if the pin, e.g. pin 132 contacts anterior region 40 and lifts hub 110 away from sizing block 62 to create a gap 142, (see FIG. 14) the practitioner is provided with an indication that the prosthetic device corresponding to pin 132 is too small for the given femur 20. In other words, a larger prosthetic device 24 would be more appropriate for attachment to the particular femur. Thus, sizing guide 48 provides the practitioner with a consistent, repeatable technique for optimizing the sizing of prosthetic devices.

It will be understood that the foregoing description is of exemplary embodiments of this invention, and that the invention is not limited to the specific form shown. For example, the sizing guide may be made of a variety of surgical grade materials in various sizes. The configuration of the stylus member as well as various other sizing features may be changed; the orientation of the opening through the sizing block may be changed, fixed or adjustable; and the sizing block may be designed for receipt of other types of rods or fixtures that allow for consistent mounting of the sizing guide relative to a fixed anatomical region. These and other modifications may be made in the design and arrangement of the elements without departing from the scope of the invention as expressed in the dependent claims.

What is claimed is:

1. A sizing guide for assisting in sizing a femoral prosthetic device during an orthopedic procedure, comprising:
   a sizing block mountable proximate a distal end of a femur at a fixed position relative to the centerline of the femoral canal, the sizing block having an opening to receive a rod extending from the femoral canal, the opening passing through the sizing block at an angle the orientation of which is adjustably selected to generally match the angle of the femoral canal relative to the distal end of the femur; and
   a stylus member movably mounted to the sizing block, the stylus member being adjustable relative to the anterior cortex of the femur to provide a size indication for the femorul prosthetic device,
   wherein the stylus member includes at least one arm with a pin thereon, the pin being capable of extending towards an anterior femur, and
   further wherein the pin is positioned at a fixed distance from a point of attachment between the stylus member and the sizing block.

2. The sizing guide as recited in claim 1, wherein the stylus member is rotatable with respect to the sizing block.

3. The sizing guide as recited in claim 1, wherein the sizing block further comprises a medial-laterial sizing feature.

4. The sizing guide as recited in claim 3, wherein the sizing block further comprises a posterior sizing feature.

5. The sizing guide as recited in claim 1, wherein the sizing block further comprises a posterior sizing feature.

6. A sizing guide for assisting in sizing a femoral prosthetic device during an orthopedic procedure, comprising:
   a sizing block mountable proximate a distal end of a femur at a fixed position relative to the centerline of the femoral canal; and
   a stylus member movably mounted to the sizing block, the stylus member being adjustable relative to the anterior cortex of the femur to provided a size indication for the femoral prosthetic device;
   wherein the stylus member is rotatable with respect to the sizing block, and
   wherein the stylus member comprises a plurality of radially extending arms having corresponding pins of differing lengths, each pin being positioned to extend toward the anterior cortex when rotated into proximity with the frame.

7. The sizing guide as recited in claim 6, wherein the position of each pin relative to the sizing block is selected to indicate a flange height of the femoral prosthetic device.

8. A sizing guide for assisting in sizing a femoral prosthetic device during an orthopedic procedure, comprising:
   a sizing block mounted to a distal cut surface of a femur, at a fixed location with respect to a femoral canal of the femur, the sizing block providing an indication of a properly sized femoral prosthetic device based on the position of the sizing block relative to the femoral canal, wherein the sizing block includes an opening for slidably receiving a rod extending from the femoral canal; and
   a rotatable stylus that may be adjusted to size the femoral prosthetic device based on the distance between the femoral canal and an anterior flange of the femoral prosthetic device,
   wherein the rotatable stylus comprises a plurality of arms of differing lengths.

9. The sizing guide as recited in claim 8, wherein the angular orientation of the opening is adjustable between at least two positions.

10. The sizing guide as recited in claim 8, further comprising a medial-laterial sizing feature to indicate medial-lateral dimensions of the femoral prosthetic device.

11. A sizing guide for assisting in sizing a femoral prosthetic device during an orthopedic procedure, comprising:
   a sizing block mounted at a fixed location with respect to a femoral canal of the femur, the sizing block providing an indication of a properly sized femoral prosthetic device based on the position of the sizing block relative to the femoral canal; and
   a rotatable stylus that may be adjusted to size the femoral prosthetic device based on the distance between the femoral canal and an anterior flange of the femoral prosthetic device,
   wherein the rotatable stylus includes a plurality of arms of differing lengths, and
   wherein a pin is coupled to each arm, the pin being oriented to extend towards an anterior region of the femur when the sizing block is at the fixed location.

* * * * *

UNITED STATES PATENT AND TRADEMARK OFFICE
CERTIFICATE OF CORRECTION

PATENT NO.    : 6,916,325 B2
DATED         : July 12, 2005
INVENTOR(S)   : Richard J. Kana et al.

It is certified that error appears in the above-identified patent and that said Letters Patent is hereby corrected as shown below:

Column 7,
Line 54, change "femorul" to -- femoral --.

Column 8,
Line 12, change "provided" to -- provide --.

Signed and Sealed this

Sixth Day of September, 2005

JON W. DUDAS
*Director of the United States Patent and Trademark Office*